US008445276B2

(12) United States Patent
Robinson et al.

(10) Patent No.: US 8,445,276 B2
(45) Date of Patent: May 21, 2013

(54) DEVICE AND METHOD FOR GROWING AND ANALYZING CELLS

(75) Inventors: Richard B. Robinson, Cresskill, NJ (US); Lev Protas, Jackson Heights, NY (US); Michael R. Rosen, New York, NY (US); Ira S. Cohen, Stony Brook, NY (US); Peter R. Brink, Setauket, NY (US)

(73) Assignees: The Trustees of Columbia in the City of New York, New York, NY (US); The Research Foundation of State University of New York, Albany, NY (US)

( * ) Notice: Subject to any disclaimer, the term of this patent is extended or adjusted under 35 U.S.C. 154(b) by 819 days.

(21) Appl. No.: 12/441,117

(22) PCT Filed: Sep. 10, 2007

(86) PCT No.: PCT/US2007/019700
§ 371 (c)(1),
(2), (4) Date: Dec. 4, 2009

(87) PCT Pub. No.: WO2008/033324
PCT Pub. Date: Mar. 20, 2008

(65) Prior Publication Data
US 2010/0075362 A1    Mar. 25, 2010

Related U.S. Application Data

(60) Provisional application No. 60/844,310, filed on Sep. 12, 2006.

(51) Int. Cl.
*C12N 5/00* (2006.01)
(52) U.S. Cl.
USPC ............................ 435/373; 435/325; 435/383
(58) Field of Classification Search .................. 435/373, 435/325, 383
See application file for complete search history.

(56) References Cited

U.S. PATENT DOCUMENTS

| 4,416,761 | A | 11/1983 | Brown et al. | |
| 5,952,191 | A * | 9/1999 | Morozov | 435/30 |
| 7,033,821 | B2 * | 4/2006 | Kim et al. | 435/288.4 |

OTHER PUBLICATIONS

Fast et al. "Cardiac tissue geometry as a determinant of unidirectional conduction block: assessment of microscopic excitation spread by optical mapping in patterned cell cultures and in a computer model", Cardioascular Research, 1995, 29:697-707.*
dictionary definition for "indentation": 1 page, 2012.*
Rothermel et al. "Cells on a chip-the use of electric properties for highly sensitive monitoring of blood-drived factors involved in angiotensin II type 1 receptor signalling", Cell Physiol Biochem, 2005, 16:51-58.*
Pijnappels et al., "Progressive Increase in Conduction Velocity Across Human Mesenchymal Stem Cells Is Mediated by Electrical Coupling," Cardiovascular Research 72 (2006): pp. 282-291.
Gaudesius, et al. "Coupling of Cardiac Electrical Activity Over Extended Distances by Fibroblasts of Cardiac Origin." Circulation Research 2003, 93:421-428.
Beeres, et al. "Human Adult Bone Marrow Mesenchymal Stem Cells Repair Experimental Conduction Block in Rat Cardiomyocyte Cultures." Journal of the American College of Cardiology, 2005, vol. 46, No. 10, pp. 1943-1952.

* cited by examiner

*Primary Examiner* — Bin Shen
(74) *Attorney, Agent, or Firm* — Evans & Molinelli PLLC; Judith A. Evans

(57) ABSTRACT

A device and method for analyzing cells includes a housing with a chamber, a barrier supported by a frame disposed within the chamber, and a plate arranged at a bottom surface of the housing interior of the chamber. The plate is adapted to receive and sustain cells and the barrier separates the plate into at least two contiguous separate areas. In some embodiments, a thin rubber strip is arranged at the bottom edge of the barrier, which facilitates control of the area in which each cell type is grown, the size of the gap between the cells, and helps prevents over growth of the two cell types on to each other.

5 Claims, 8 Drawing Sheets

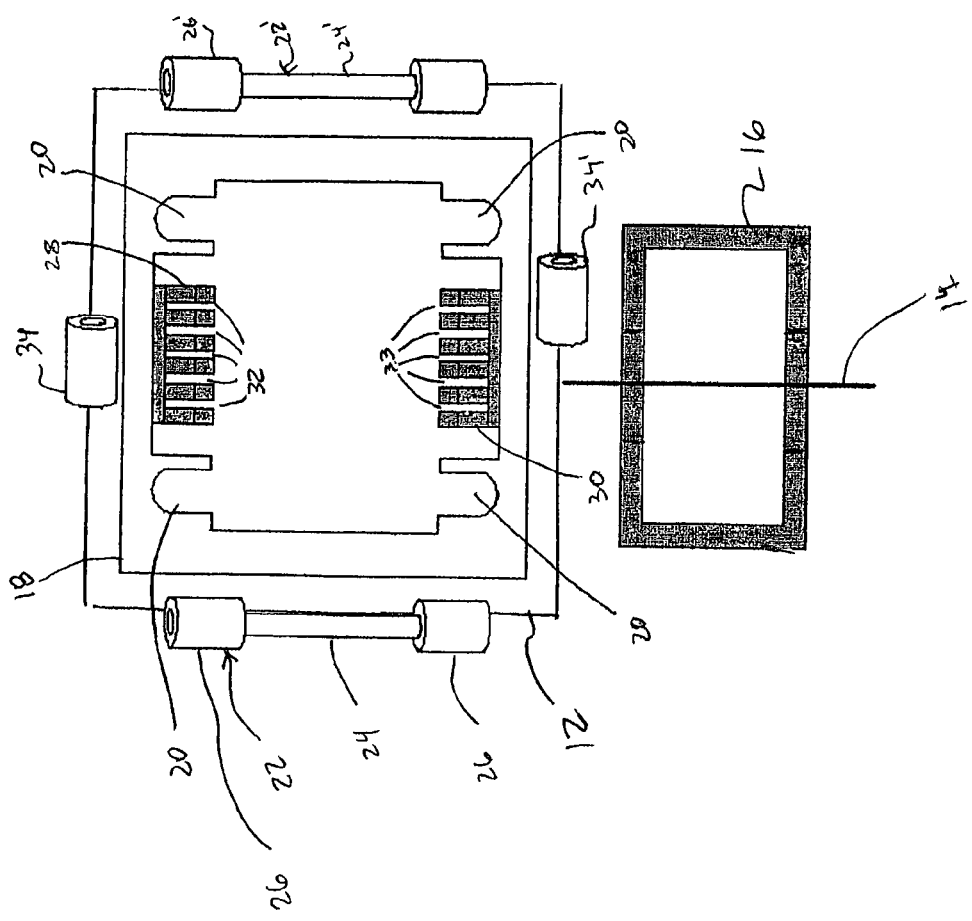
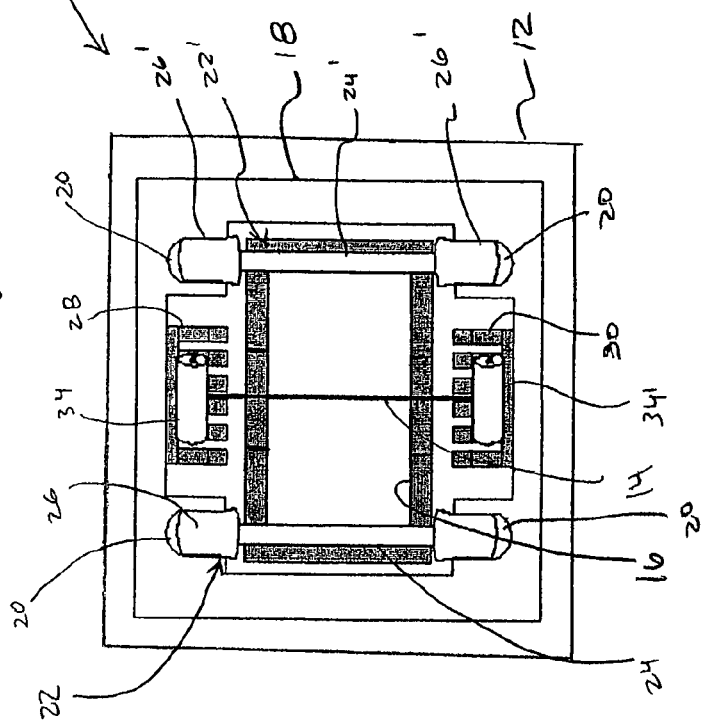
Figure 1
Figure 2

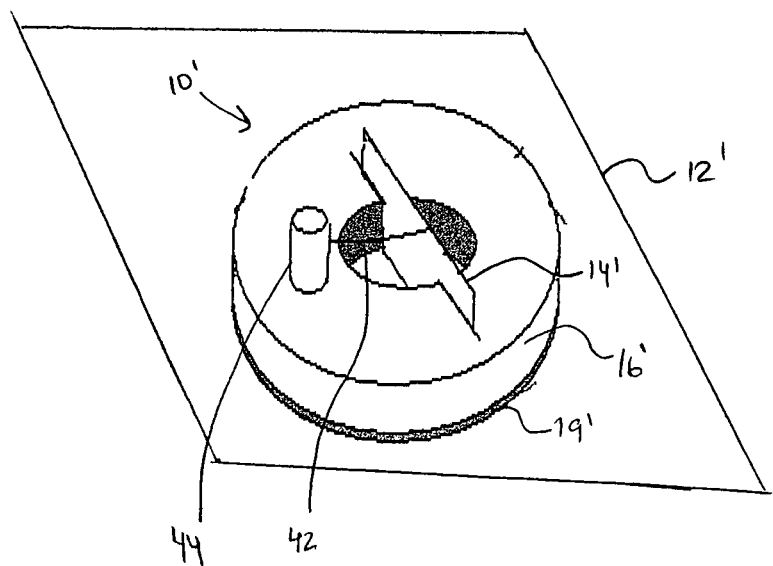

DEVICE AND METHOD FOR GROWING AND ANALYZING CELLS

FIELD OF THE INVENTION

The present invention relates to a device and method for growing and analyzing cells, e.g., in at least two areas on a cell culture separated by a removable barrier.

BACKGROUND INFORMATION

It is conventional to conduct studies of the interrelationships between two or more cell types grown in the same culture dish or between two regions of the same cell type that have been differentially treated, e.g., by over expression of a gene in one region only. Pijnappels et al. describe physically disrupting an existing monolayer of one cell type and then adding a second layer of another cell type over the disrupted area. Pijnappels et al., "Progressive Increase in Conduction Velocity Across Human Mesenchymal Stem Cells Is Mediated by Electrical Coupling," *Cardiovasc Research* (2006), doi:10.1016/j.cardiores.2006.07.016.

There is believed to be a need for device and method for studying the interrelationships between two or more cell types grown in the same culture dish or between two regions of the same cell type that have been differentially treated without physically disrupting the cells.

SUMMARY

An example embodiment of the present invention includes a housing with a chamber, a barrier disposed within the chamber, and a rubber seal adhered to a bottom surface of the housing where it contacts the plate. The plate is adapted to receive and sustain cells and the barrier separates the plate into at least two separate areas.

A rubber strip may be placed between a bottom edge of the barrier and the plate. The rubber strip may be adhered to the bottom edge of the barrier. The rubber strip allows for the area in which each cell type is grown and the size of the gap between the cells to be controlled and over growth of the two cell types on to each other avoided.

The plate may include a multichannel electrode array (MEA), for example, an MEA produced by Multi Channel Systems, in Reutlingen, Germany.

The device may include a frame disposable within the chamber. The frame may include a slot adapted to accommodate the barrier.

The device may include locking members adapted to frictionally engage and secure the frame within the housing.

The locking members may be adapted to apply a downward force on the frame so as to create a seal between the frame and the plate. The downward force may be sufficient to prevent cell growth across the barrier but not high enough to leave an indentation on the plate.

The device may include locking members adapted to frictionally engage and secure the barrier within the housing.

The locking members may include rubber members adapted to be wedged between the housing and the frame.

The locking members may include screws.

The locking members may include flat set screws that pass through the housing at an angle and press against the frame forcing it downward against the plate.

An exemplary device for use with a plate adapted to receive and sustain cells according to the present invention includes a removable barrier and housing with a chamber. The removable barrier may be disposed within the chamber, adapted to seal against the plate, and separate the plate into at least two contiguous separate areas.

An exemplary method of the present invention includes: a) placing a barrier on a plate so as to divide the plate into at least two separate areas; b) forming cells on the plate on opposite sides of the barrier; c) removing the barrier; and d) detecting at least one parameter of the cells after removing the barrier.

The at least one parameter may include an electrical activity of the cells.

The barrier may be forced against the plate at a predetermined pressure, which, for example, may be sufficient to prevent cell growth across the barrier but not so high as to leave an indentation on the plate.

A study may be conducted of the interrelationships between two or more cell types grown in the same culture dish or between two regions of the same cell type that have been differentially treated without physically disrupting the cells being analyzed.

The time course interaction as the cell types grow together may be monitored.

One cell type may be monitored while an adjacent cell type, on an opposite side of the barrier prior to its removal, is selectively exposed to a source or agent, which may have an effect on the cells, e.g., drugs.

The conduction across and between multiple cell types may be measured, for example, using an MEA.

The device may be used as a test system for experiments intended for the development and improvement of AV node bypass.

Example embodiments of the present invention are described in more detail below with reference to the appended Figures. The foregoing description and examples have been set forth merely as illustrative and are not intended as being limiting. Each of the disclosed aspects and embodiments may be considered individually or in combination with other aspects, embodiments, and variations thereof. The steps of the methods described herein are not confined to any particular order of performance.

BRIEF DESCRIPTION OF THE DRAWINGS

FIG. 1 is a top view of a device according to an exemplary embodiment of the present invention.

FIG. 2 illustrates the device of FIG. 1 with the locks, frame and barrier removed and placed to the side of the device housing.

FIG. 10 is a perspective view of an exemplary embodiment of the present invention not including a housing.

DETAILED DESCRIPTION

Figure 3:
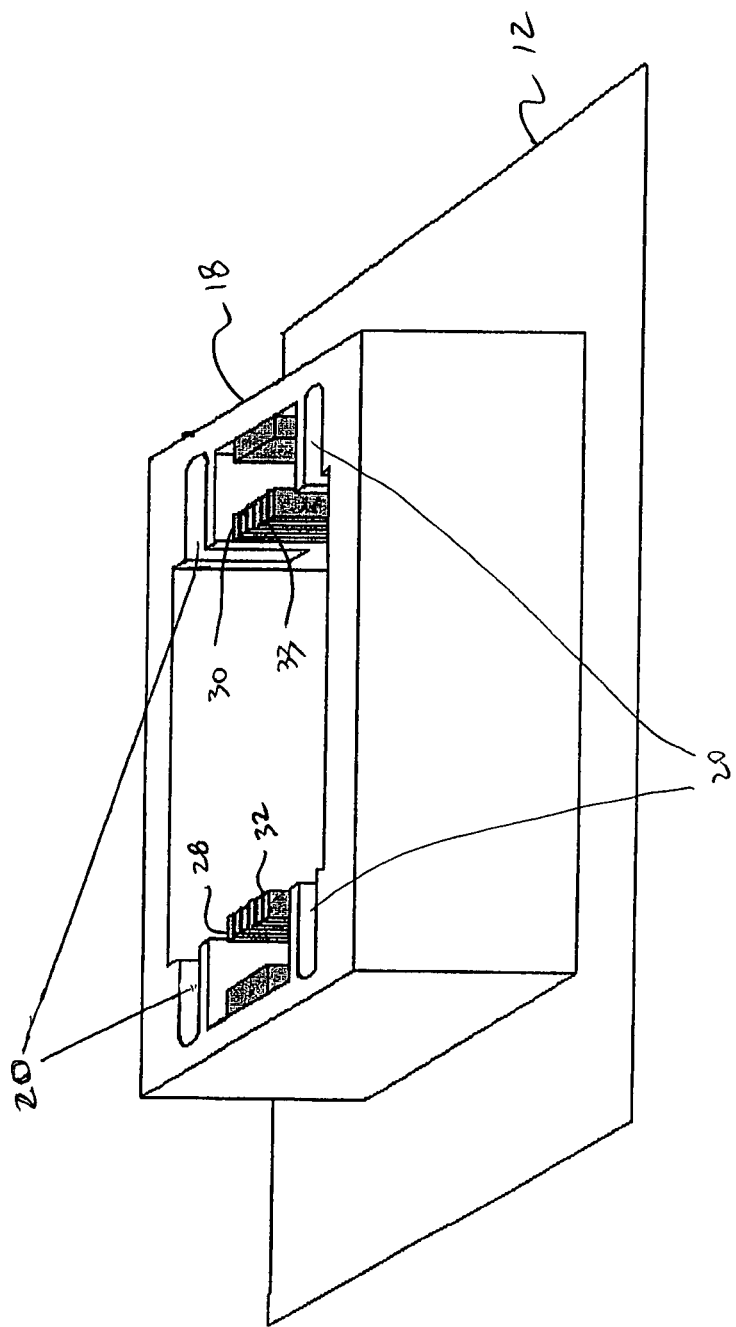
FIG. 3 is a perspective view of the device illustrated in FIG. 1 with the frame and barrier removed.
Figure 4:
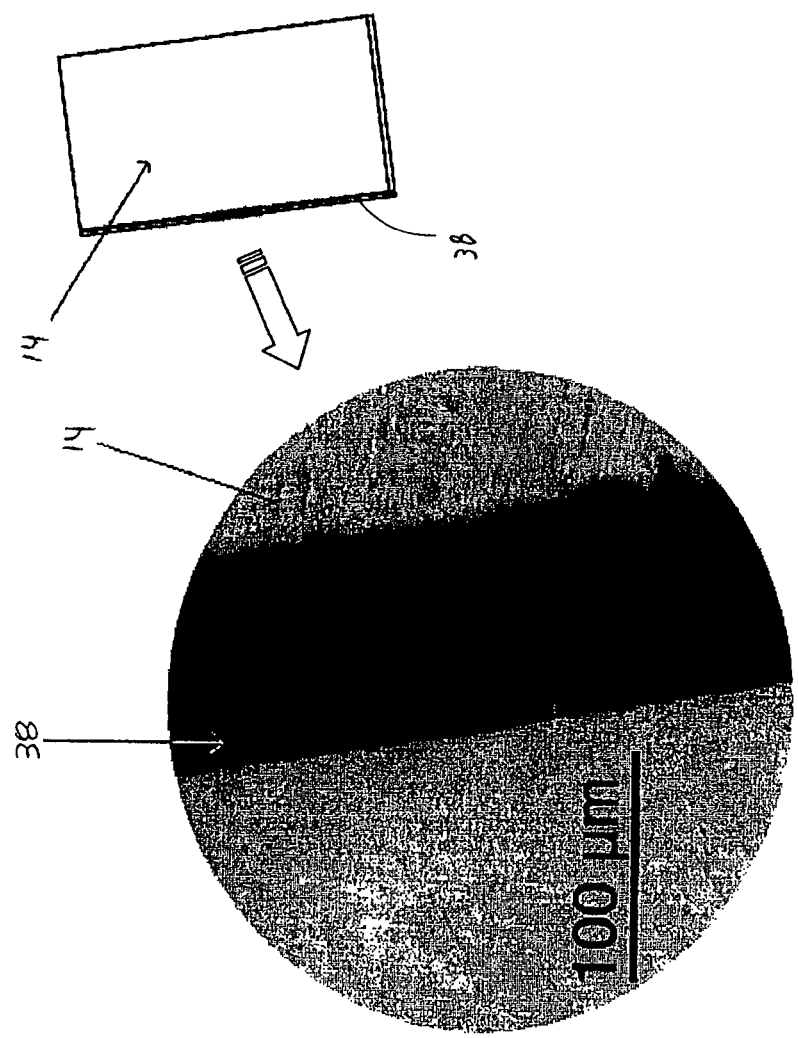
FIG. 4 is a perspective view of the divider and a magnified view of the rubber strip on the bottom edge of the divider.

As illustrated in the top view of FIG. 1, an exemplary embodiment the present invention, generally designated 10, is designed to facilitate studies of the interrelationships between two or more cell types grown in the same culture dish, i.e., on plate 12, or between two regions of the same cell type that have been differentially treated, e.g., by over expression of a gene in one region only. Monolayers of the studied cells are separated by a thin barrier 14 at the time of initial plating. The barrier is subsequently removed leaving in place a gap on the plate 12 between cells on the plate that is suitable to allow opposing groups of cells to grow across it and make physical contact with each other.

The device 10 may be used to test the response of one cell type to pharmacologic agents administered only to the adjacent cell type, since the separation of the two cell types allows the use of a perfusion arrangement that restricts drug exposure to only a portion of the total area, even after the barrier 14 is removed. The device 10 may also be used for modeling of specific arrhythmia mechanisms, e.g., reentry. Such modeling can be used to facilitate an understanding of the likelihood that various interventions, including pharmaceuticals, will suppress or induce arrhythmias.

A frame 16 is placed inside a housing 18, which is placed over plate 12. The housing 18 has recesses 20, which accommodate locks 22 used to secure frame 16 to housing 18. Locks 22, 22' include an elongate member 24, 24' capped on opposite ends with a high friction member 26, 26', for example, made from rubber. Locks 22, which may be adjustable in length, are sized to frictionally engage housing 18 to mechanically fix frame 16 in place in the housing 18. Housing 18 also includes opposing rack members 28, 30 which include slots 32, 33 for receiving one or more of the barriers 14 at various positions along the length of the housing 18. The use of more than one barrier 14 allows for the study of more than two kinds of cells. Locks 34, 34' also made from a high friction material, such as rubber, are used to secure barrier 14 in place within slots 32 by frictionally engaging opposing members 28, 30 and side edges of barrier 14. The frame 16, housing 18, and rack members 28, 30 may be made from conventional materials, for example, from a plastic such as polystyrene or polycarbonate. All parts of the device can be easily sterilized, e.g., using alcohol.

Figure 5:
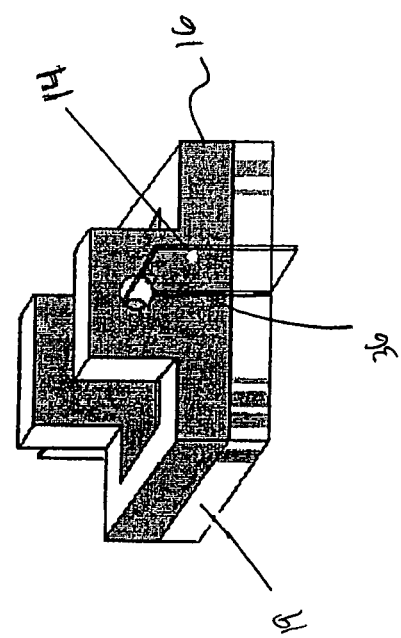
FIG. 5 is a perspective view of the frame illustrated in FIGS. 1 and 2.

FIG. 2 illustrates the device 10 in a disassembled state with the locks 22, 22', 34, 34' and frame 16 placed to the side of the housing 18. As illustrated in FIG. 5, the frame 16 includes a slot 36 to accommodate the barrier 14 and is mounted to the plate 12 using a layer 19 of glue or sealing material, such as a 2 mm thick layer of Sylgard-184, for example, adhered to the frame 16 but not the plate 12. The frame 16 restricts the area of the growing cells and prevents leakage of media and cells around the side edges of the barrier 14. Any space between the barrier 14 and the frame 16 in slot 36 may be filled, for example, with a glue such as Sylgard-184. Frame 16 also allows for easy management of barrier 14 which, given its thin structure, may be difficult to hold and manipulate without damage.

Figure 8:
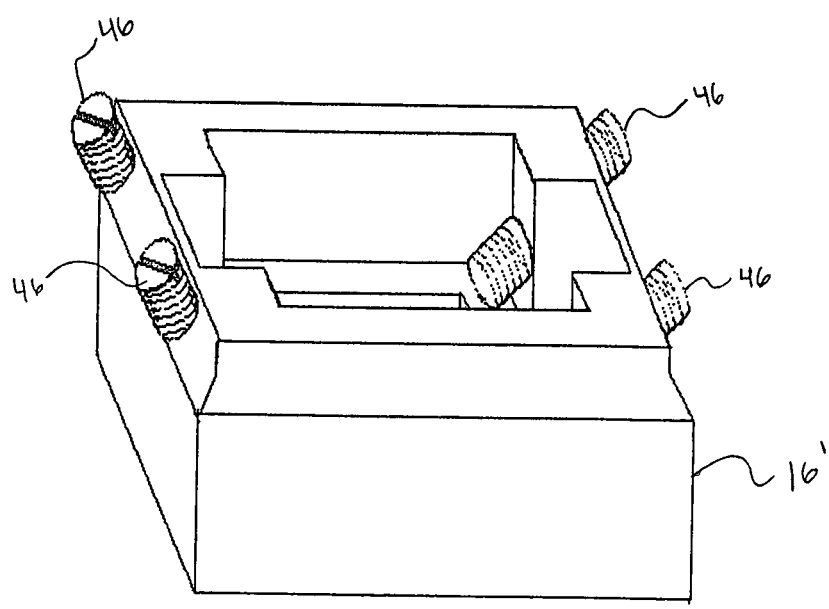
FIG. 8 is a perspective view of an exemplary embodiment of the housing including screws.

Housing 18 may be removably fixed to a separate support member, i.e., a table, or may be removably fixed to the plate 12 over a portion not used for cell growth. The housing 18 is fixed so that it can be used for leverage to create a downward force on the frame 16 to create a seal between the frame 16 and the plate 12. The downward force may be created, for example, using locks 22, 22' or using screws. Screws may be passed in an upward angled direction through a bottom of the housing into the frame effectively pulling the frame downwardly toward the plate 12. Alternatively, flat tipped set screws may be passed through holes in the housing 18 so as to press against the frame 16 and bear down against it at a predetermined pressure so as to create a seal between the frame 16 and the plate 12. A frame 16' including set screws 46 is illustrated in FIG. 8.

Plate 12 may be any substrate suitable for cell culture and may include a multichannel electrode array (MEA) system (Multi Channel Systems, Reutlingen, Germany). The use of an MEA allows for the measurement of conduction across and between multiple cell types. Alternatively, conduction across and between the cell types may be measured using voltage sensitive dyes or other methods for recording electrical events.

Barrier 14 may be made from a glass sheet, e.g., a commercial 9×18 mm coverslip, for example, having thickness of 100 or 120 micrometers, or any other suitable rigid and thin material. Barrier 14 provides a seal on the surface of plate 12 to assure that the cell lines are separated. Barrier 14 may include a thin strip of softer material 38, such as rubber, to assure that it does not scratch or otherwise alter the surface of the plate 12. The thin strip of softer material 38 may be formed by covering a Teflon plate with a thin layer of sil-poxi-glue (silicone rubber adhesive, Smooth-On Inc., Easton, Pa.) and vertically mounting a bottom edge of the barrier 14 (the one which sits on the plate 12) on the thin layer of the sil-poxi-glue. After allowing the rubber to harden, e.g., for 15 to 20 minutes, the barrier 14 is removed from the Teflon plate by cutting the glue along both sides of the barrier 14 edge. This procedure may be repeated to increase the thickness of the rubber strip, for example, up to a thickness of 100 micrometers. The rubber strip adheres tightly to the barrier 14 thus allowing the barrier to be reused multiple times.

Figure 9:
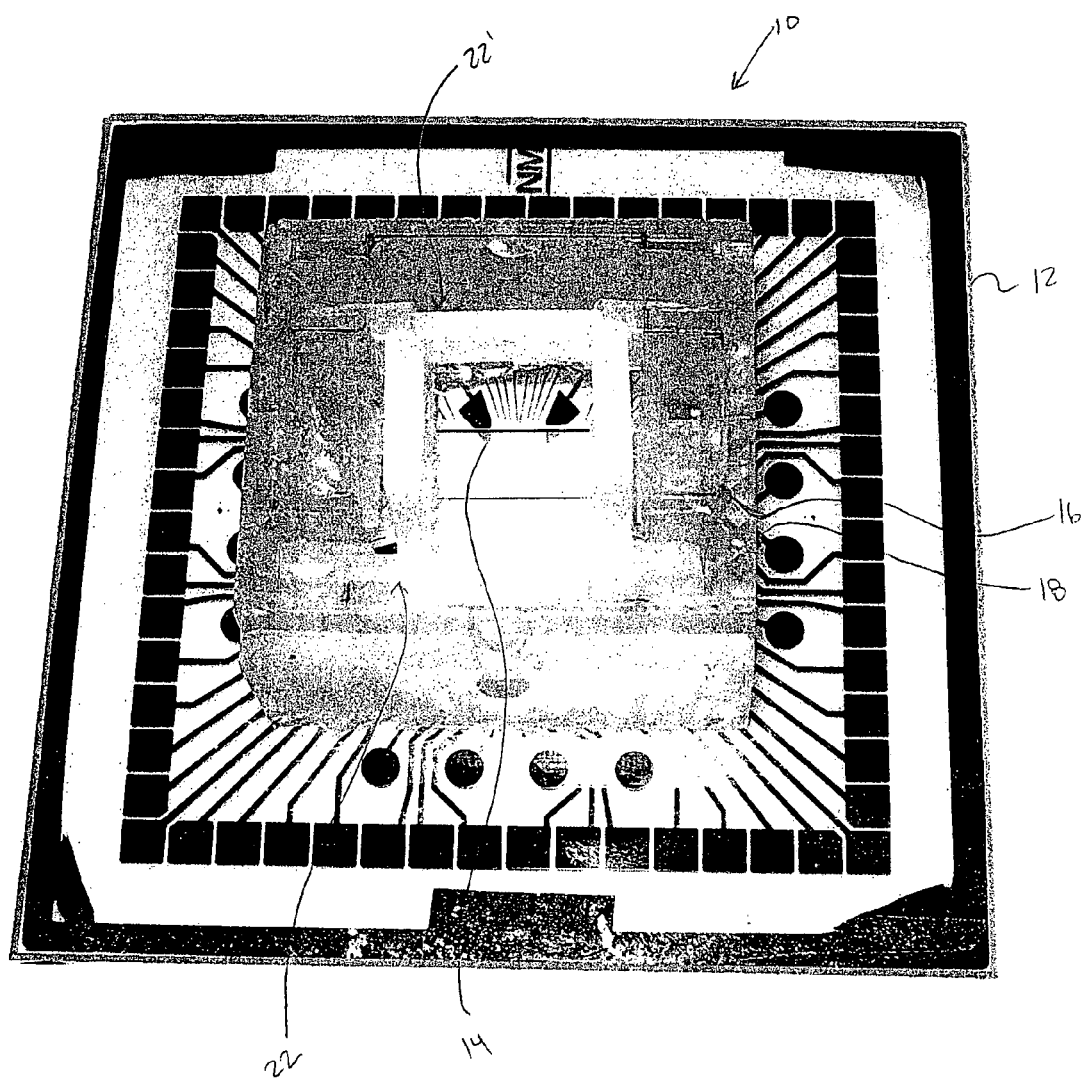
FIG. 9 is a photograph of a device according to an exemplary embodiment of the present invention.

FIG. 9 is a photograph of device 10 over an MEA shown without locking members 34, 34'.

Figure 6:
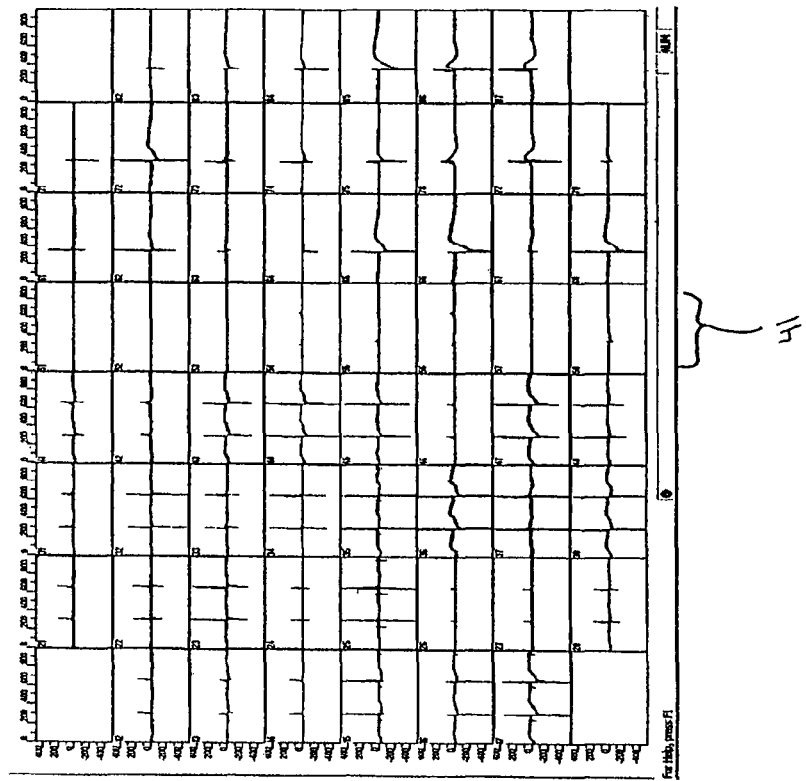
FIG. 6 is a grid including plots of the action potential of cardiomyocyte cells at multiple locations on an MEA plate 24 hours after removal of the barrier.
Figure 7:
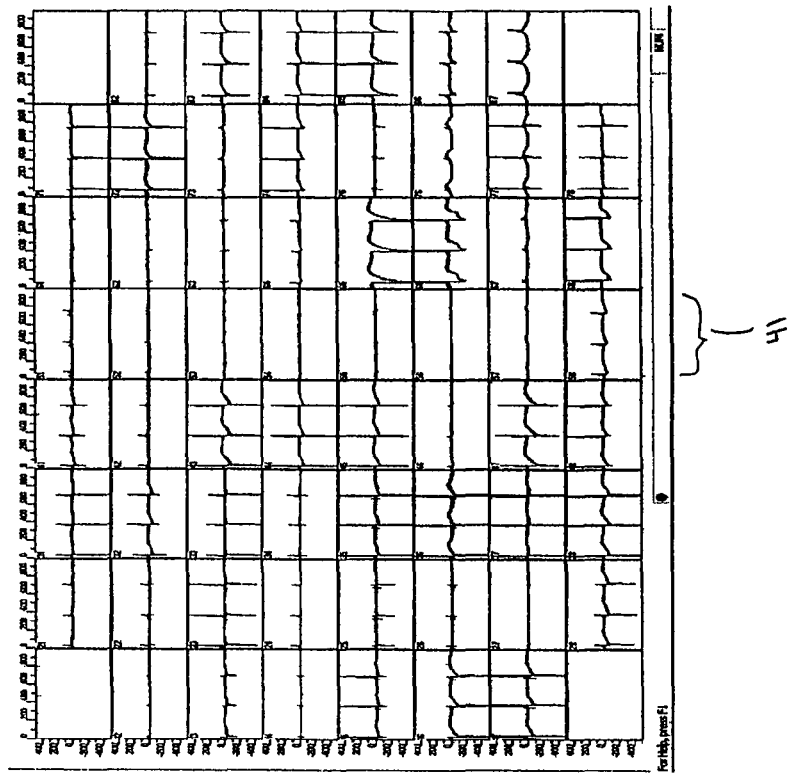
FIG. 7 is the grid of FIG. 6 but showing action potential plots of cardiomyocyte cells 72 hours after removal of the barrier.

The device 10 may be used as follows. Cardiomyocyte cells are plated and cultured on an MEA plate 12 inside the housing 18 with the glass barrier 14 in place. The MEA is used to record the electrical activity of the cells, e.g., from sixty points in the culture area, for example, three days after the cells are plated and the barrier 14 is removed. Within, e.g., 24 hours after removing the barrier 14, the two areas of cells on opposite sides of the barrier 14 may have different rate and timing of action potentials. Within, e.g., 72 hours after the barrier 14 is removed, both cell areas may have synchronized action potentials, which means that they develop physical and functional contacts. FIG. 6 is a grid including multiple plots of the action potentials of the cardiomyocyte cells occupied by the cells 24 hours after removing the barrier 14 at 60 different locations along the plate 12, and FIG. 7 is similar grid including multiple plots of the action potentials 72 hours after removing the barrier 14. Each box or cell of the grid in FIGS. 6 and 7 (except for the corners) includes a plot of electrical activity, i.e., extracellular potential (y-axis), over time (x-axis). The grids include plots for each of the 60 monitored cell areas on the plate's multichannel electrode array. No electrical activity is observed in FIG. 6 in the column labeled 41 since this column represents the location at which the barrier 14 is placed, indicating that cells do not bridge the gap after twenty four hours.

In an exemplary embodiment of the device 10' illustrated in FIG. 10, the frame 16' may be connected or adhered to the plate 12' without a housing, using, for example, screws, or as illustrated, using an adhesive 19', such as Sylgard-184. The frame 16' may be made, for example, from plastic. A spring 42, for example, made from metal or fiberglass, is supported on a post 44 and used to bear pressure against the barrier 14' so as to press it against the frame 16' and the plate 12' below. Alternatively, the frame 16' may be made from Sylgard-184, which is set, for example, in a mold using a removable insert to form the slit for the barrier 14' and the center space used for cell growth.

What is claimed is:

1. A method, comprising:
   a) providing a removable barrier comprising a strip formed from a soft material of a predetermined thickness arranged on a bottom edge of a barrier,
   b) placing the removable barrier on a plate such that the strip contacts the plate thereby dividing the plate into at least two separate areas;
   c) forming cells on the plate in the at least two separate areas on opposite sides of the barrier;
   d) removing the barrier after forming the cells; and
   e) detecting at least one parameter of the cells on the plate after removing the barrier.

2. The method of claim 1, wherein the at least one parameter includes an electrical activity of the cells.

3. The method of claim 1, further comprising forcing the barrier against the plate at a predetermined pressure.

4. The method of claim 3, wherein the pressure is sufficient to prevent cell growth across the barrier without leaving an indentation on the plate.

5. The method of claim 1 wherein the soft material is rubber.

* * * * *